United States Patent
Jacquin et al.

(10) Patent No.: US 11,261,168 B2
(45) Date of Patent: Mar. 1, 2022

(54) PROCESS FOR SYNTHESIZING 5-HYDROXYMETHYLFURFURAL

(71) Applicant: IFP Energies nouvelles, Rueil-Malmaison (FR)

(72) Inventors: Marc Jacquin, Lyons (FR); Damien Delcroix, St. Maurice l Exil (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/961,184

(22) PCT Filed: Dec. 21, 2018

(86) PCT No.: PCT/EP2018/086707
§ 371 (c)(1),
(2) Date: Jul. 9, 2020

(87) PCT Pub. No.: WO2019/137810
PCT Pub. Date: Jul. 18, 2019

(65) Prior Publication Data
US 2021/0053930 A1    Feb. 25, 2021

(30) Foreign Application Priority Data
Jan. 10, 2018    (FR) ..................... 1850210

(51) Int. Cl.
*C07D 307/44*    (2006.01)
(52) U.S. Cl.
CPC ................. *C07D 307/44* (2013.01)

(58) Field of Classification Search
CPC .................................................. C07D 307/44
See application file for complete search history.

(56) References Cited

U.S. PATENT DOCUMENTS

| 4,590,283 | A | 5/1986 | Gaset et al. |
| 10,239,852 | B2 | 3/2019 | Souleymanou et al. |
| 10,421,735 | B2 * | 9/2019 | Souleymanou ...... C07D 307/50 |
| 10,526,302 | B2 * | 1/2020 | Souleymanou ...... C07D 307/50 |
| 10,662,167 | B2 * | 5/2020 | Kunz .................. C07D 307/46 |

FOREIGN PATENT DOCUMENTS

| FR | 2669635 A1 | 5/1992 |
| WO | 17016924 A1 | 2/2017 |

OTHER PUBLICATIONS

Zhen Huang et al: "Triazaheterocyclic compound as an efficient catalyst for dehydration of fructose into 5-hydroxymethylfurfural", RSC Advances, vol. 4, No. 26, Jan. 1, 2014 (Jan. 1, 2014), pp. 13434, XP055473049, DOI: 10.1039/c4ra00534a.
International Search Report PCT/2018EP/086707 (pp. 1-2) dated Mar. 22, 2019.

* cited by examiner

*Primary Examiner* — Golam M Shameem
(74) *Attorney, Agent, or Firm* — Millen, White, Zelano & Branigan, PC; Ryan Pool

(57) ABSTRACT
The invention relates to a process for synthesizing 5-hydroxymethylfurfural from a fructose-containing feedstock in the presence of at least one aprotic polar solvent and at least one dehydration catalyst, in which process the maximum instantaneous fructose concentration 5.0 wt %.

16 Claims, No Drawings

PROCESS FOR SYNTHESIZING 5-HYDROXYMETHYLFURFURAL

TECHNICAL FIELD OF THE INVENTION

The invention relates to a particular process for the conversion of sugars, more specifically hexoses and more specifically fructose, into 5-hydroxymethylfurfural (hereinafter denoted by the abbreviation 5-HMF) in the presence of at least one polar aprotic solvent and in the presence of one or more catalysts.

PRIOR ART

5-Hydroxymethylfurfural is a compound derived from biomass which can be given economic value in many fields, as precursor of active principles in the pharmaceutical industry, agrochemistry or specialty chemistry. Its advantage in recent years lies in its use as precursor of 2,5-furandicarboxylic acid (FDCA), which is used as substitute for terephthalic acid as monomer in the production of polyester fibers, convenience plastics or plasticizers.

The production of 5-HMF by dehydration of hexoses has been known for many years and has been the subject of a large number of research studies.

Mention may in particular be made of the studies which were carried out on the dehydration of sugars in polar aprotic solvents. More particularly still, mention may be made of the studies which were carried out on the dehydration of sugars in dimethyl sulfoxide (DMSO): the selectivity for conversion of the sugars into 5-HMF is particularly good therein, and it is possible to operate to complete conversion of the sugars (absence of side rehydration reaction of 5-HMF to give formic acid and levulinic acid).

Nevertheless, it is well known that the distillation of solutions of 5-HMF in DMSO is problematic. Thus, separation techniques other than distillation have to be envisaged, such as that described in the patent FR 2 669 635. In this patent, a description is given of a process for the liquid/liquid extraction of 5-HMF contained in DMSO, by addition of water and of an organic solvent, such as dichloromethane or diethyl ether, for example. The cost of this separation is inversely proportional to the concentration of 5-HMF in the DMSO (reduction in the flow rates of water and of solvent which are necessary, reduction in the number of stages of the liquid/liquid extractor which are necessary, for example). It is thus advantageous to be able to produce, from sugar, a solution of 5-HMF in DMSO which is as concentrated as possible.

When the protocols described in the literature are repeated at higher initial concentrations of sugars, a significant loss in selectivity is recorded with in particular the formation of byproducts which cannot be given economic value and which cannot be recycled, such as humins. For example, in RSC Adv., 2014, 4, 13434, Xu et al. describe the dehydration of fructose in DMSO in the presence of HCl at 5% by weight of fructose in DMSO and at 30% by weight of fructose in DMSO. By thus increasing the concentration of the fructose feedstock in DMSO, the molar yield of 5-HMF falls from 88% to 69%. In point of fact, the high cost of the feedstocks envisaged resulting from sacchariferous biomasses does not allow the slightest loss in selectivity. Furthermore, the presence of byproducts, such as humins, complicates the process for the extraction of the 5-HMF as described in the patent FR 2 669 635 (partial precipitation of the humins by addition of water, requiring a filtration stage). This greatly limits the attractiveness of this route for the synthesis and extraction of 5-HMF, in particular for the purpose of operating the process on the industrial scale.

The aim of the invention is consequently to overcome the disadvantages of the prior art. An aim of the invention is in particular to improve the production of 5-HMF in DMSO and more particularly to produce, with a high degree of selectivity, a highly concentrated solution of 5-HMF in DMSO, while having a high productivity. A subsidiary aim of the invention is to facilitate the extraction of the 5-HMF from said solution as a result of its high concentration.

Definitions and Abbreviations

Instantaneous fructose concentration is understood to mean the concentration of monomeric fructose measured at any moment in the reaction mixture and which corresponds to the ratio by weight of the weight of monomeric fructose present in the reaction medium to the weight of reaction solvent at this same moment of the reaction.

Selectivity is understood to mean the ratio of the number of moles of 5-HMF produced to the number of converted moles of fructose which is contained in the feedstock introduced into the process.

Productivity is understood to mean the number of moles of 5-HMF produced per hour and per weight of reaction solvent, expressed in mol/(h*kg).

Final 5-HMF concentration is understood to mean the ratio of the weight of 5-HMF to the weight of reaction solvent.

Homogeneous catalyst is understood to mean a catalyst which is soluble in the reaction medium. Heterogeneous catalyst is understood to mean a catalyst which is insoluble in the reaction medium.

Brønsted acid is understood to mean a molecule of the family of the Brønsted acids which can release a proton H+ in the reaction medium.

Inorganic catalyst is understood to mean a catalyst in which the functional group responsible for the catalytic dehydration activity is not bonded to a hydrocarbon chain by a covalent bond.

Inorganic Brønsted acid catalyst is understood to mean a Brønsted acid catalyst which does not contain carbon atoms and which can release a proton H+ in the reaction medium.

Inorganic Lewis acid catalyst is understood to mean a Lewis acid catalyst containing an atom from the family of metals or lanthanides.

Aprotic solvent is understood to mean a molecule which acts as solvent and all the hydrogens of which are carried by carbon atoms.

Polar solvent is understood to mean a molecule which acts as solvent, the dipole moment p of which, expressed in debye units, has a numerical value of greater than or equal to 2.00, measured at 25° C.

Polar aprotic solvent is thus understood to mean a molecule which acts as solvent, all the hydrogens of which are carried by carbon atoms and the dipole moment p of which, expressed in debye units, has a numerical value of greater than or equal to 2.00, measured at 25° C.

wt % denotes a percentage by weight.

SUBJECT MATTER OF THE INVENTION

The invention relates to a process for the production of 5-hydroxymethylfurfural (5-HMF) which comprises bringing a fructose-containing saccharide feedstock into contact, in a polar aprotic solvent, with at least one dehydration catalyst chosen from homogeneous or heterogeneous and organic or inorganic Brønsted acids and Lewis acids, said process being carried out at a temperature of between 30° C. and 175° C. and at a pressure of between 0.0001 MPa and 8.0 MPa, in which the instantaneous fructose concentration is less than or equal to 5.0 wt %.

Advantageously, the combination of the different parameters of the process according to the invention, in particular the control of the instantaneous fructose concentration, makes it possible to obtain 5-HMF with a very good yield and an excellent selectivity and is accompanied by an improvement in productivity.

DETAILED DESCRIPTION OF THE INVENTION

Feedstock

The fructose-containing saccharide feedstock employed in the process according to the invention comprises fructose or any saccharide feedstock which contains fructose, either in the free fructose form or in the form of a monomeric, oligomeric or polymeric fructoside saccharide unit which can release fructose by a hydrolysis stage. Preferentially, the feedstock treated in the process is fructose.

Advantageously, the fructose-containing saccharide feedstock comprises fructose in monomeric, oligomeric or polymeric form.

Feedstock containing free fructose denotes, for example, fructose, pure fructose syrups or else syrups of High-Fructose Corn Syrup type containing fructose and glucose in different proportions (glucose/fructose in ratios by weight or by moles 58/42, 45/55, 10/90, for example). Syrup is understood to mean a solution of sugar in water having a concentration of at least 30 wt %, preferably at least 50 wt %, preferably at least 70 wt %.

Sugar feedstock containing fructose in monomeric, oligomeric or polymeric fructoside form denotes the oligosaccharides and polysaccharides in which at least one monosaccharide unit is fructose. Feedstocks such as sucrose, kestose, fructans, oligofructans or inulin are denoted, for example.

Advantageously, the saccharide feedstocks are capable of releasing monomeric fructose by glycoside hydrolysis, said fructose produced being able to be converted into 5-HMF.

Oligosaccharide more particularly denotes a carbohydrate having the empirical formula $(C_{6m}H_{10m+2}O_{5m+1})(C_{5n}H_{8n+2}O_{4n+1})$, where m and n are integers, the sum of which is between 2 and 6. The monosaccharide units making up said oligosaccharide are identical or different and at least one unit of formula $(C_{6m}H_{10m+2}O_{5m+1})$ is fructose. By extension, polysaccharide denotes a carbohydrate having the empirical formula $(C_{6m}H_{10m+2}O_{5m+1})(C_{5n}H_{8n+2}O_{4n+1})$, where m and n are integers, the sum of which is greater than or equal to 7.

Advantageously, in the case where the feedstock does not contain only fructose but also glucose, the process according to the invention can make it possible to produce a mixture of 5-HMF and glucose. For example, in the case where the feedstock is sucrose, the process according to the invention can make it possible to produce an equimolar mixture of 5-HMF and glucose. Likewise, in the case where the feedstock is High-Fructose Corn Syrup, the process according to the invention makes it possible to produce a mixture of 5-HMF and glucose, the stoichiometry of which depends on the composition of the starting High-Fructose Corn Syrup.

The feedstock is introduced into the process in a solvent/feedstock ratio by weight of between 0.1 and 200.0, preferably between 0.3 and 100.0 and more preferentially between 1.0 and 50.0.

Solvents

The process according to the invention is carried out in the presence of at least one polar aprotic solvent. The polar aprotic solvent is advantageously chosen from butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate and γ-valerolactone. Preferably, the polar aprotic solvent is chosen from acetone, hexamethylphosphoramide, N,N-dimethylformamide, sulfolane, N-methylpyrrolidone, dimethyl sulfoxide, propylene carbonate and γ-valerolactone. Preferably, the polar aprotic solvent is dimethyl sulfoxide (DMSO).

Dehydration Catalyst

According to the invention, the process is carried out in the presence of at least one dehydration catalyst chosen from homogeneous or heterogeneous and organic or inorganic Brønsted acids and Lewis acids capable of catalyzing the dehydration of fructose to give 5-hydroxymethylfurfural.

In one embodiment, at least one dehydration catalyst is chosen from homogeneous or heterogeneous organic Brønsted acids capable of catalyzing the dehydration of fructose to give 5-hydroxymethylfurfural.

Preferably, the homogeneous organic Brønsted acid catalysts are chosen from organic acids of general formulae R'COOH, R'SO$_2$H, R'SO$_3$H, (R'SO$_2$)NH, (R'O)$_2$PO$_2$H, R'OH, in which R' is chosen from the following groups:

alkyls, preferably comprising between 1 and 15 carbon atoms, preferably between 1 and 10 and preferably between 1 and 6, which are or are not substituted by at least one substituent chosen from a hydroxyl, an amine, a nitro, a halogen, preferably fluorine, and an alkyl halide, alkenyls, which are or are not substituted by at least one group chosen from a hydroxyl, an amine, a nitro, an oxo, a halogen, preferably fluorine, and an alkyl halide, aryls comprising between 5 and 15 carbon atoms and preferably between 6 and 12 carbon atoms, which are or are not substituted by a substituent chosen from a hydroxyl, an amine, a nitro, an oxo, a halogen, preferably fluorine, and an alkyl halide, heteroaryls comprising between 4 and 15 carbon atoms and preferably between 4 and 12 carbon atoms, which are or are not substituted by a substituent chosen from a hydroxyl, an acid, an amine, a nitro, an oxo, a halogen, preferably fluorine, and an alkyl halide.

When the catalysts of organic Brønsted acid type are chosen from organic acids of general formula R'—COOH, R' can also be a hydrogen.

Preferably, the organic Brønsted acids are chosen from formic acid, acetic acid, trifluoroacetic acid, lactic acid, levulinic acid, 2,5-furandicarboxylic acid, methanesulfinic acid, methanesulfonic acid, trifluoromethanesulfonic acid, bis(trifluoromethanesulfonyl)amine, benzoic acid, para-toluenesulfonic acid, 4-biphenylsulfonic acid, diphenyl phosphate and 1,1'-binaphthyl-2,2'-diyl hydrogen phosphate. Very preferably, the homogeneous organic Brønsted acid catalyst is chosen from methanesulfonic acid ($CH_3SO_3H$) and trifluoromethanesulfonic acid ($CF_3SO_3H$).

The heterogeneous organic Brønsted acid catalysts are chosen from ion-exchange resins, in particular from sulfonic acid resins based on a copolymer preferably of sulfonated styrene/divinylbenzene or on a sulfonated tetrafluoroethylene copolymer (such as, for example, the following commercial resins: Amberlyst® 15, 16, 35 or 36, Dowex® 50 WX2, WX4 or WX8, Nafion® PFSA NR-40 or NR-50, or Aquivion® PFSA PW 66, 87 or 98), charcoals functionalized by sulfonic and/or carboxylic groups, or silicas functionalized by sulfonic and/or carboxylic groups. Preferably, the heterogeneous organic Brønsted acid catalyst is chosen from sulfonic acid resins.

In one embodiment, at least one dehydration catalyst is chosen from homogeneous inorganic Brønsted acids and homogeneous or heterogeneous inorganic Lewis acids capable of catalyzing the dehydration of fructose to give 5-hydroxymethylfurfural.

Preferably, the homogeneous inorganic Brønsted catalysts are chosen from HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40}).xH_2O$, $H_4SiMo_{12}O_{40}$, $H_3PMo_{12}O_{40}$, $(NH_4)_6Mo_7O_{24}.xH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$ and $HIO_3$. Preferably, the inorganic Brønsted acids are chosen from HCl, HBr, HI, $H_2SO_4$, $H_3PO_4$ or $HNO_3$. Very preferably, the inorganic Brønsted acid is HCl.

Preferably, the inorganic dehydration catalyst is chosen from homogeneous inorganic Lewis acids corresponding to the general formula (II) $M_oX_p$, which are or are not solvated, in which:

M is an atom chosen from lithium or the atoms of Groups 3 to 16, preferably 6 to 13, of the Periodic Table, lanthanides included, and preferably from Li, B, Al, Fe, Zn, Sn, Cr, Ce or Er, and preferably from Li, Al, Sn or Cr, o is an integer between 1 and 10, preferably between 1 and 5 and preferably between 1 and 2, p is an integer between 1 and 10, preferably between 1 and 5 and preferably between 1 and 3, and X is an anion chosen from halides, alkylsulfonates, perhaloalkylsulfonates or bis(perhaloalkylsulfonyl)amides, preferably X is chosen from halides chosen from $Cl^-$, $Br^-$ and $I^-$, alkylsulfonates or perhaloalkylsulfonates, it being possible for said anions X to be identical or different in the case where o is greater than 1.

Very preferably, the homogeneous inorganic Lewis acids are chosen from LiCl, $BF_3$, $AlCl_3$, $FeCl_2$, $ZnCl_2$, $SnCl_2$, $CrCl_3$, $CeCl_3$, $Al(OTf)_3$ and $ErCl_3$. Very preferably, the homogeneous inorganic Lewis acid is chosen from LiCl, $Al(OTf)_3$ and $AlCl_3$.

The heterogeneous inorganic Lewis acids are chosen from simple or mixed oxides of the compounds chosen from silicon, aluminum, zirconium, titanium, niobium and tungsten, which are undoped or doped with an element chosen from tin, tungsten and hafnium, and from metal phosphates, said metals being chosen from niobium, zirconium, tantalum, tin and titanium. Preferably, the heterogeneous Lewis acids are chosen from zirconium oxides, titanium oxides, mixed oxides of aluminum and of silicon doped with tin, such as the zeolite Sn-β or the mesostructured silica Sn-MCM-41, tin phosphates and titanium phosphates.

The dehydration catalyst(s) are introduced into the reaction mixture in a solvent/catalyst(s) ratio by weight of between 20 and 10 000, preferably between 40 and 2000, preferably between 100 and 1000, in which the weight of solvent corresponds to the total weight of solvent employed in the process.

In a specific embodiment, the process is carried out with at least two dehydration catalysts, in which at least one of the two catalysts is a chlorine-comprising catalyst. Preferably, said chlorine-comprising catalyst is chosen from HCl, LiCl, $AlCl_3$, $FeCl_3$, $ZnCl_2$, $SnCl_2$, $CrCl_3$, $CeCl_3$ and $ErCl_3$.

Implementation of the Process

Preferably, said process is carried out at a temperature of between 30° C. and 175° C., preferably between 40° C. and 150° C., preferably between 45° C. and 130° C., preferably between 50° C. and 120° C., preferably between 50° C. and 100° C., preferably between 55° C. and 95° C., preferably between 60° C. and 90° C., preferably between 60° C. and 85° C., preferably between 60° C. and 80° C., very preferably between 65° C. and 75° C., and at a pressure of less than 8 MPa, preferably of between 0.0001 and 8.0 MPa, preferably between 0.001 and 5.0 MPa, preferably between 0.001 and 4.0 MPa, preferably between 0.001 and 3.5 MPa and preferably between 0.01 and 3.0 MPa.

According to the invention, the process is characterized in that the instantaneous fructose concentration in the reaction mixture is less than or equal to 5.0 wt %, preferably less than or equal to 4.5 wt %, preferably less than or equal to 4.0 wt %, preferably less than or equal to 3.5 wt %, preferably less than or equal to 3.0 wt %, preferably less than or equal to 2.5 wt %, preferably less than or equal to 2.0 wt %, preferably less than or equal to 1.5 wt % and preferably less than or equal to 1.0 wt %. Preferably, the instantaneous concentration is between 0.001 and 5.0 wt %, preferably between 0.001 and 4.5 wt %, preferably between 0.001 and 4.0 wt %, preferably between 0.001 and 3.5 wt %, preferably between 0.001 and 3.0 wt %, preferably between 0.001 and 2.5 wt %, preferably between 0.001 and 2.0 wt %, preferably between 0.001 and 1.5 wt %, very preferably between 0.001 and 1.0 wt %.

The maintenance of the instantaneous fructose concentration can be obtained by any means known to a person skilled in the art. Preferably, the maintenance of the instantaneous fructose concentration is controlled by measurement of the instantaneous fructose concentration during the implementation of the process according to the invention. Said measurement can be carried out by any methods known to a person skilled in the art and preferably by high-performance liquid chromatography (HPLC).

The maintenance of the instantaneous concentration in accordance with the invention is obtained by controlling the amount of fructose in the reaction medium. Said control can be obtained by the use of an oligosaccharide or polysaccharide feedstock which limits said instantaneous concentration as a function of the rate of hydrolysis of the oligosaccharide or polysaccharide to give monosaccharides. Said control can also be obtained by adjusting the feeding with feedstock into the reaction mixture as a function of the instantaneous fructose concentration measured.

Advantageously, the control of the instantaneous fructose concentration makes it possible to obtain an excellent selectivity for 5-HMF and also an improvement in productivity.

Said feeding into the reaction mixture can be carried out according to several forms of introduction of said feedstock.

In a first embodiment, the feedstock is introduced into the reaction mixture in the solid form, using a suitable device which makes it possible to control the flow rate of feedstock. Nonlimitingly, this device can be an endless screw or a pneumatic system for the transportation of solid particles. Nonlimitingly, this embodiment is preferred for a feedstock of oligosaccharide or polysaccharide type.

The introduction of a feedstock in the solid form corresponding to sucrose, to kestose or to inulin, from which fructose is gradually released by hydrolysis, is one possibility. Said introduction can be carried out one or more times, sequentially, or else continuously, in order to maintain an instantaneous fructose concentration of less than or equal to 5.0 wt %, preferably of less than or equal to 4.5 wt %, preferably of less than or equal to 4.0 wt %, preferably of less than or equal to 3.5 wt %, preferably of less than or equal to 3.0 wt %, preferably of less than or equal to 2.5 wt %, preferably of less than or equal to 2.0 wt %, preferably of less than or equal to 1.5 wt % and preferably of less than or equal to 1.0 wt %.

In a second embodiment, the feedstock is introduced in the liquid form into the reaction medium in solution in a solvent, known as additional solvent, using a pump which makes it possible to control the flow rate for introduction of the feedstock-containing solution. The choice of the additional solvent which makes it possible to dissolve the feedstock is then essential in obtaining a high final concentration of 5-HMF. This embodiment is particularly well suited to a feedstock of monosaccharide type, indeed even oligosaccharide type, which can be dissolved in the additional solvent at high concentrations.

Preferably, the gradual introduction of a feedstock corresponding to a fructose syrup or a fructose and glucose syrup (of High-Fructose Corn Syrup type) via a pump is carried out. Said introduction can be carried out one or more times, sequentially, or else continuously, as long as the instantaneous fructose concentration is kept less than or equal to 5.0 wt %, preferably less than or equal to 4.5 wt %, preferably less than or equal to 4.0 wt %, preferably less than or equal to 3.5 wt %, preferably less than or equal to 3.0 wt %, preferably less than or equal to 2.5 wt %, preferably less than or equal to 2.0 wt %, preferably less than or equal to 1.5 wt % and preferably less than or equal to 1.0 wt %.

Additional Solvent

In a second specific embodiment, the process also comprises the use of at least one additional solvent chosen from polar aprotic or protic solvents. Preferably, said additional solvent is chosen from butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate, γ-valerolactone, water, methanol, ethanol, formic acid and acetic acid.

Preferably, the additional solvent chosen from polar aprotic or protic solvents is acetone, hexamethylphosphoramide, N,N-dimethylformamide, sulfolane, N-methylpyrrolidone, dimethyl sulfoxide, propylene carbonate, γ-valerolactone, water, methanol and ethanol, preferably from N,N-dimethylformamide, sulfolane, N-methylpyrrolidone, dimethyl sulfoxide, water and methanol, and very preferably the additional solvent is chosen from water and dimethyl sulfoxide.

In this second embodiment, the final concentration of 5-HMF cannot exceed the solubility limit of the sugar in the additional solvent, modified by the molar mass ratio of the fructose to the 5-HMF and modified by the dilution of the feedstock by the mass of polar aprotic solvent.

In a third embodiment, the additional solvent used corresponds to all or to a fraction of the reaction mixture. In this scenario, the additional solvent thus contains at least the polar aprotic solvent, at least one dehydration catalyst employed in the process and optionally at least a fraction of unconverted feedstock of the 5-HMF produced. This embodiment advantageously makes it possible to gradually increase the amount of 5-HMF without increasing the volume of additional solvent. This embodiment of the process for the production of 5-HMF is carried out non-continuously.

In a continuous implementation of the process according to the invention, the weight hourly space velocity (flow rate of feedstock by weight/weight of catalysts) is between 0.01 $h^{-1}$ and 5.0 $h^{-1}$ and preferably between 0.02 $h^{-1}$ and 2.0 $h^{-1}$.

Whatever the embodiment of the process employed, the water contained in the reaction mixture is preferably removed by any methods known to a person skilled in the art, preferably continuously, in order to maintain a water content of less than 30.0 wt %, with respect to the total weight of solvent, preferably of less than 20.0 wt %, preferably of less than 15.0 wt % and very preferably of less than 10.0 wt %.

Advantageously, the implementation of the process for the production of 5-HMF, in particular by the control of the instantaneous concentration, makes it possible to obtain a good conversion of the fructose involved, and also an excellent selectivity in favor of 5-HMF, and to improve the 5-HMF productivity.

Thus, the selectivity, yield and productivity obtained by the implementation of the process according to the invention make it possible, for example, to achieve final concentrations by weight of 5-HMF of greater than 3.5 wt %. The process according to the invention advantageously makes it possible to achieve final concentrations by weight of 5-HMF of greater than 5.0 wt %, preferably of greater than 10 wt % and very preferably of greater than 15 wt %.

The Products Obtained and Their Method of Analysis

The product selectively obtained by the conversion process according to the invention is 5-hydroxymethylfurfural (5-HMF). On conclusion of the reaction carried out in the process according to the invention, the reaction medium is analyzed by gas chromatography (GC) in order to determine the 5-HMF content in the presence of an internal standard and by liquid chromatography in order to determine the conversion of the feedstock in the presence of an external standard and in order to quantify the undesired products, such as levulinic acid, formic acid and any coproduct containing sugars. The humins are quantified by difference in carbon balance with the carbon initially introduced.

EXAMPLES

In the examples below, the fructose used as feedstock is commercially available and is used without further purification.

The hydrochloric acid is used in the form of a concentrated 1.0M (mol/l) commercial solution in diethyl ether. The methanesulfonic acid, denoted MSA in the examples, is commercially available and is used without further purification.

The dimethyl sulfoxide and the N-methylpyrrolidone, respectively denoted DMSO and NMP in the examples, used as polar aprotic solvents, are commercially available and are used without further purification.

The preparation of the thiourea 1 employed in example 3 is described in the patent application WO2017/016924 A1.

In the examples below, the degree of conversion of the fructose to give 5-HMF is total. The selectivity for 5-HMF revealed can thus be compared to the yield of the conversion process. The productivity is expressed in mmol of 5-HMF which are formed per kilogram of solvent and per hour.

Example 1 (Not in Accordance) Conversion of the Fructose to Give 5-HMF in the Presence of Hydrochloric Acid With [Fructose]$_0$=9.0 wt %

Hydrochloric acid (1.0 M in Et$_2$O) (200 µl equivalent to 0.007 g, 0.19 mmol) is added to a solution of fructose (2.0 g, 11.10 mmol) in DMSO (20.0 g). The initial fructose concentration is 9.0 wt %. The solvent/catalyst ratio by weight is 2857. The reaction medium is stirred at 70° C. for 12 h. The conversion of the fructose to give 5-HMF is monitored by regularly taking samples of an aliquot of solution which is instantly cooled to 0° C., dissolved in water and checked by liquid chromatography. The selectivity for 5-HMF after 12 h is 90.0%. The concentration by weight of the 5-HMF in the DMSO at the end of the reaction is 5.7 wt %. The yield of undesired humins is 5.0%. The associated productivity is 41.6 mmol/kg/h.

Example 2 (Not in Accordance) Conversion of the Fructose to Give 5-HMF in the Presence of Hydrochloric Acid With [Fructose]$_0$=30.0 wt %

Hydrochloric acid (1.0 M in Et$_2$O) (200 µl equivalent to 0.007 g, 0.19 mmol) is added to a solution of fructose (8.6 g, 47.73 mmol) in DMSO (20.0 g). The initial fructose concentration is 30.0 wt %. The solvent/catalyst ratio by weight is 2857. The reaction medium is stirred at 70° C. for 24 h. The conversion of the fructose to give 5-HMF is obtained by taking a sample of an aliquot of solution at the end of the test which is instantly cooled to 0° C., dissolved in water and checked by liquid chromatography. The selectivity for 5-HMF after 24 h is 70.0%. The concentration by weight of the 5-HMF in the DMSO at the end of the reaction is 14.7 wt %. The yield of undesired humins is 25.0%. The associated productivity is 69.6 mmol/kg/h.

Example 3 (Not in Accordance) Conversion of a Mixture of Glucose and Fructose to Give 5-HMF in the Presence of Thiourea 1 With [Fructose]$_0$=4.6 wt %

The thiourea 1 (0.046 g, 0.12 mmol) is added to a solution of glucose (1.0 g, 5.55 mmol) and fructose (1.0 g, 5.55 mmol) in NMP (20.0 g). The initial fructose concentration is 4.6 wt %. The solvent/catalyst ratio by weight is 435. The reaction medium is stirred at 120° C. for 6 h. The conversion of the fructose to give 5-HMF is monitored by regularly taking samples of an aliquot of solution which is instantly cooled to 0° C., dissolved in water and checked by liquid chromatography. The selectivity for 5-HMF after 6 h is 52.2%. The molar yield of 5-HMF after 6 h is 58.0%. The concentration by weight of the 5-HMF in the NMP at the end of the reaction is 3.0 wt %. The yield of undesired humins is 25.0%. The associated productivity is 53.7 mmol/kg/h.

Example 4 (in Accordance) Conversion of the Fructose to Give 5-HMF in the Presence of Hydrochloric Acid With [Fructose]$_{inst}$ Kept Less Than or Equal to 1.0 wt %

Hydrochloric acid (1.0 M in Et$_2$O) (200 µl equivalent to 0.007 g, 0,19 mmol) is added to 5.0 g of DMSO, which constitutes the initial reaction medium. The initial fructose concentration is 0 wt % in this medium. The reaction medium is thermostatically controlled at 70° C. A syringe containing a 12.0 wt % solution of fructose in 15.0 g of DMSO is added to the initial reaction medium at the rate of a flow rate of 4.0 ml/h for 4 hours. The total solvent/catalyst ratio by weight is 2857. At the end of the addition, the reaction medium is maintained at 70° C. for a further 1 hour. The instantaneous fructose concentration in the reaction mixture during reaction is checked by liquid chromatography and is less than or equal to 1.0 wt %. The 5-HMF yield is obtained by taking a sample of an aliquot of solution at the end of the test which is instantly cooled to 0° C., dissolved in water and checked by liquid chromatography. The selectivity for 5-HMF after 5 h is 99.5%. The final concentration of 5-HMF in the DMSO at the end of the reaction is 6.7 wt %. The yield of undesired humins is 0.5%. The associated productivity is 113.4 mmol/kg/h.

Example 5 (in Accordance) Conversion of the Fructose to Give 5-HMF in the Presence of Hydrochloric Acid With [Fructose]$_{inst}$ Kept Less Than or Equal to 1.0 wt %

Hydrochloric acid (1.0 M in Et$_2$O) (670 µl equivalent to 0.023 g, 0,64 mmol) is added to 10.0 g of DMSO, which constitutes the initial reaction medium. The initial fructose concentration is 0 wt % in this medium. The reaction medium is thermostatically controlled at 70° C. A syringe containing a 32.0 wt % solution of fructose in 140.0 g of DMSO is added to the initial reaction medium at the rate of a flow rate of 8.0 ml/h for 16 hours. The total solvent/catalyst ratio by weight is 6521. At the end of the addition, the reaction medium is maintained at 70° C. for a further 2 hours. The instantaneous fructose concentration in the reaction mixture during reaction is checked by liquid chromatography and is less than or equal to 1.0 wt %. The 5-HMF yield is obtained by taking a sample of an aliquot of solution at the end of the test which is instantly cooled to 0° C., dissolved in water and checked by liquid chromatography. The selectivity for 5-HMF after 18 h is 99.0%. The concentration by weight of the 5-HMF in the DMSO at the end of the reaction is 21.0 wt %. The yield of undesired humins is 1.0%. The associated productivity is 134.1 mmol/kg/h.

Example 6 (Not in Accordance) Conversion of the Fructose to Give 5-HMF in the Presence of Methanesulfonic Acid With [Fructose]$_0$=9.0 wt %

Methanesulfonic acid (0.018 g, 0.19 mmol) is added to a solution of fructose (2.0 g, 11.10 mmol) in DMSO (20.0 g). The initial fructose concentration is 9.0 wt %. The solvent/catalyst ratio by weight is 1111. The reaction medium is stirred at 70° C. for 12 h. The conversion of the fructose to give 5-HMF is monitored by regularly taking samples of an aliquot of solution which is instantly cooled to 0° C., dissolved in water and checked by liquid chromatography. The selectivity for 5-HMF after 12 h is 74.0%. The final concentration of 5-HMF in the DMSO at the end of the reaction is 4.7 wt %. The yield of undesired humins is 10.0%. The associated productivity is 34.2 mmol/kg/h.

Example 7 (in Accordance) Conversion of the Fructose to Give 5-HMF in the Presence of Methanesulfonic Acid With [Fructose]$_{inst}$ Kept Less Than or Equal to 1.0 wt %

Methanesulfonic acid (0.018 g, 0.19 mmol) is added to 5.0 g of DMSO, which constitutes the initial reaction medium. The initial fructose concentration is 0 wt % in this medium. The reaction medium is thermostatically controlled at 70° C. A syringe containing a 12.0 wt % solution of fructose in 15.0 g of DMSO is added to the initial reaction medium at the rate of a flow rate of 4.0 ml/h for 4 hours. The total solvent/catalyst ratio by weight is 1111. At the end of the addition, the reaction medium is maintained at 70° C. for a further 1 hour. The instantaneous fructose concentration in the reaction mixture during reaction is checked by liquid chromatography and is less than or equal to 1.0 wt %. The 5-HMF yield is obtained by taking a sample of an aliquot of solution at the end of the test which is instantly cooled to 0° C., dissolved in water and checked by liquid chromatography. The selectivity for 5-HMF after 5 h is 88.0%. The final concentration of 5-HMF in the DMSO at the end of the reaction is 5.6 wt %. The yield of undesired humins is 3.0%. The associated productivity is 100.3 mmol/kg/h.

The selectivity for 5-HMF is greater in the case where the instantaneous fructose concentration is kept less than 5.0 wt % and in particular in the examples less than 1.0 wt %.

The final concentration by weight of 5-HMF accessible by the process according to the invention is greater in the case where the instantaneous fructose concentration is kept less than 4.0 wt % and in particular in the examples less than 1.0 wt %.

The yield of undesired products, such as humins, is lower in the case where the instantaneous fructose concentration is kept less than 4.0 wt % and in particular in the examples less than 1.0 wt %.

The 5-HMF productivity, expressed in mmol of 5-HMF produced per kg of solvent and per hour (mmol/kg/h), is greater in the case where the instantaneous fructose concentration is kept less than 4.0 wt % and in particular in the examples less than 1.0 wt %.

It is thus apparent, unexpectedly, that it is markedly advantageous to keep the instantaneous fructose concentration in accordance with the invention in order to achieve very good selectivities, high concentrations by weight of 5-HMF, greater productivities and low yields of undesired products in the conversion of sugars to give 5-HMF, in comparison with a conversion where the instantaneous fructose concentration is not controlled.

The invention claimed is:

1. A process for the production of 5-hydroxymethylfurfural comprising
bringing at least one fructose-containing saccharide feedstock into contact, in at least one polar aprotic solvent, with at least one dehydration catalyst chosen from homogeneous or heterogeneous and organic or inorganic Brønsted acids and Lewis acids,
said process being carried out at a temperature of between 30° C. and 175° C. and at a pressure of between 0.0001 MPa and 8.0 MPa, wherein the instantaneous fructose concentration is less than or equal to 4.0 wt %.

2. The process of claim 1, wherein the instantaneous fructose concentration is less than 3.5 wt %.

3. The process of claim 1, wherein the maintenance of the instantaneous fructose concentration is obtained by the sequential or continuous introduction of the feedstock.

4. The process of claim 3, wherein the feedstock is introduced in the liquid form in the presence of an additional solvent selected from the group consisting of butan-2-one, acetone, acetic anhydride, N,N,N', N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate, γ-valerolactone, water, methanol, ethanol, formic acid and acetic acid.

5. The process of claim 3, wherein the feedstock is introduced in the liquid form in the presence of an additional solvent corresponding to a fraction or to all of the reaction mixture.

6. The process of claim 1, wherein the temperature is between 40° C. and 150° C.

7. The process of claim 1, wherein the saccharide feedstock comprises fructose in monomeric, oligomeric or polymeric form.

8. The process of claim 1, wherein the feedstock is chosen from fructose, sucrose, kestose, fructans, oligofructans or inulin.

9. The process of claim 1, wherein the feedstock is introduced in a solvent/feedstock ratio by weight of between 0.1 and 200.

10. The process of claim 1, wherein the polar aprotic solvent is selected from the group consisting of butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate and γ-valerolactone.

11. The process of claim 1, wherein the polar aprotic solvent is dimethyl sulfoxide.

12. The process of claim 1, wherein the homogeneous organic Brønsted acid catalysts are selected from the group consisting of organic acids of formulae R'COOH, R'SO$_2$H, R'SO$_3$H, (R'SO$_2$)NH, (R'O)$_2$PO$_2$H, R'OH, in which R' is chosen from the following groups:
alkyls, which are or are not substituted by at least one substituent selected from the group consisting of a hydroxyl, an amine, a nitro, a halogen, a fluorine, and an alkyl halide,
alkenyls, which are or are not substituted by at least one group selected from the group consisting of a hydroxyl, an amine, a nitro, an oxo, a halogen, a fluorine, and an alkyl halide,
aryls, which are or are not substituted by a substituent selected from the group consisting of a hydroxyl, an amine, a nitro, an oxo, a halogen, a fluorine, and an alkyl halide,
heteroaryls, which are or are not substituted by a substituent selected from the group consisting of a hydroxyl, an amine, a nitro, an oxo, a halogen, a fluorine, and an alkyl halide.

13. The process of claim 1, wherein the homogeneous inorganic Brønsted catalysts are selected from the group consisting of HF, HCl, HBr, HI, H$_2$SO$_3$, H$_2$SO$_4$, H$_3$PO$_2$, H$_3$PO$_4$, HNO$_2$, HNO$_3$, H$_2$WO$_4$, H$_4$SiW$_{12}$O$_{40}$, H$_3$PW$_{12}$O$_{40}$, (NH$_4$)$_6$(W$_{12}$O$_{40}$).xH$_2$O, H$_4$SiMo$_{12}$O$_{40}$, H$_3$PMo$_{12}$O$_{40}$, (NH$_4$)$_6$Mo$_7$O$_{24}$.xH$_2$O, H$_2$MoO$_4$, HReO$_4$, H$_2$CrO$_4$, H$_2$SnO$_3$, H$_4$SiO$_4$, H$_3$BO$_3$, HClO$_4$, HBF$_4$, HSbF$_5$, HPF$_6$, H$_2$FO$_3$P, ClSO$_3$H, FSO$_3$H, HN(SO$_2$F)$_2$ and HIO$_3$.

14. The process of claim 1, wherein the dehydration catalyst(s) are introduced in a solvent/catalyst(s) ratio by weight of between 20 and 10 000, wherein the weight of solvent corresponds to the total weight of solvent employed in the process.

15. The process of claim 1, wherein at least two dehydration catalysts are employed and wherein at least one of the catalysts is a chlorine-comprising catalyst.

16. The process of claim 12 wherein the alkyls are comprised of between 1 and 15 carbon atoms, the aryls are comprises of between 5 and 15 carbon atoms, and the heteroaryls are comprises of between 4 and 15 carbon atoms.

* * * * *